United States Patent
Ravo et al.

[11] Patent Number: 6,117,148
[45] Date of Patent: Sep. 12, 2000

[54] INTRALUMINAL ANASTOMOTIC DEVICE

[76] Inventors: Biagio Ravo, Rome America Hospital via Emilio Longoni, 69 - Rome, Italy, 00155; Enrico Nicolo, 1515 Timberlane, Clairton, Pa. 15025

[21] Appl. No.: 09/173,867

[22] Filed: Oct. 16, 1998

Related U.S. Application Data

[60] Provisional application No. 60/062,281, Oct. 17, 1997.

[51] Int. Cl.⁷ .................................................. A61B 17/04
[52] U.S. Cl. ..................... 606/153; 227/180.1; 227/181.1
[58] Field of Search .................................. 606/219, 220; 227/19, 179–181.1

[56] References Cited

U.S. PATENT DOCUMENTS

| | | | |
|---|---|---|---|
| 4,606,343 | 8/1986 | Conta et al. | 227/180 |
| 4,848,367 | 7/1989 | Avant et al. | 227/179 |
| 4,893,622 | 1/1990 | Green et al. | 227/180 |
| 5,139,513 | 8/1992 | Segato | 606/219 |
| 5,197,648 | 3/1993 | Gingold | 227/179 |
| 5,355,897 | 10/1994 | Pietrafitta et al. | 227/180 |
| 5,639,008 | 6/1997 | Gallagher et al. | 227/175.1 |

OTHER PUBLICATIONS

Ravo, Biagio, M.D., "Perineal Transanal Colonic Resection: An Experimental Study", Reprinted from "Diseases of the Colon & Rectum", vol. 29, No. 1, 1986.

*Primary Examiner*—Gary Jackson
*Attorney, Agent, or Firm*—Webb Ziesenheim Logsdon Orkin & Hanson, P.C.

[57] ABSTRACT

An intestinal intraluminal reconstruction and resection device includes a mechanism for intussusception of the bowel, a bowel anastomosis mechanism and a mechanism for severing the resected bowel. The surgical device allows the user to carry out intraluminally an anastomosis first, prior to resection of the intestine or any hollow viscus, therefore not exposing the dirty intraluminal content to the clean abdominal or thoracic cavities. The above is achieved by first intussuscepting the hollow viscus, then anastomosis and finally intraluminal resection.

20 Claims, 6 Drawing Sheets

INTRALUMINAL ANASTOMOTIC DEVICE

This application claims the benefit of U.S. Provisional Patent Application Ser. No. 60/062,281 filed Oct. 17, 1997 entitled "Intraluminal Anastomotic Device", which is incorporated herein by reference.

BACKGROUND OF THE INVENTION

1. Field of the Invention

We, Biagio Ravo and Enrico Nicolo, have developed improvements which relate to the field of surgery and, particularly, our invention relates to a hollow viscus (intestine, vascular, urinary, etc.) resection and reconstruction device for hollow viscus surgery. The following discussion will relate to colon surgery, but the same can be applied in any hollow viscus surgery.

2. Background Information

The techniques of resecting a segment of the colon or intestine and an anastomosis of the cut ends are common procedures where a segment of diseased bowel must be removed for reasons such as inflammation, oncological process, obstructions, bleeding, perforation, trauma, etc. A conventional procedure for resection and anastomosis operates as follows. The first step is mobilization of a segment to be resected. Mobilization is achieved by freeing the intestine from its cavity attachment and is then followed by separating its blood supply. The mobilization can be conducted laparoscopically or through opening the peritoneal cavity. Second, resection of the segment to be removed follows the mobilization procedure. Often in removing the interior segment, the lumen of the bowel is opened, exposing the contaminated area to the clean peritoneal cavity, increasing the risk of postoperative complications. Following the resection of the segment to be removed, the remaining ends of the bowel are anastomosed to guarantee the continuity of the intestinal track.

Complications can occur in such procedures because, at times, the anastomosis can rupture for various reasons and can leak into the peritoneal cavity increasing the morbidity and mortality rate of such procedures. See Biagio Ravo "Colorectal Anastomotic Healing and Intercolonic Bypass Procedure". Surgical Clinic North America 1988;68(6), Pages 1267–1294.

Techniques are a major factor in maintaining the integrity of an anastomosis. Multiple techniques are described in the literature to achieve this goal. However, studies have shown that leakage rates remain substantially constant between mechanical and suture techniques.

The intestine is like a tunnel communicating with the outside environment through the mouth and the anus, therefore making its luminal contents contaminated. The bowel wall separates the contaminated interior area from the clean area of the peritoneal cavity. Complications can occur when the bowel wall is compromised which allows communication between the contaminated area within the bowel and the clean area outside the bowel within the peritoneal cavity. With this understanding, the lumen of the intestine is exterior to the body. It is possible to resect any piece of the intestinal wall from the lumen without ever communicating the dirty intraluminal content to the clean peritoneal cavity, assuming that the bowel has been mobilized from its attachments. This has already been disclosed in an experimental study, "Perineal Transanal Colonic Resection: An Experimental Study" by Biagio Ravo, M.D. et al., in *Diseases of the Colon & Rectum,* January 1986, Vol. 29, No. 1. In this study conducted on dogs, the colon was intussuscepted through the anus to the desired length followed by resection and anastomosis of the colon outside the clean body cavity. The intussusception of the colon at the anus allows the resection to be conducted outside the body cavity, preventing contamination of the body cavity.

The same resection of the colon as described above can be performed higher up in the lumen of the colon by using the technique of intussusception of the segment of the colon to be removed. This technique was described at our Scientific Exhibit, American College of Surgeons in June 1995. The difficulty with the proposed procedure to be applied to any part of the exterior track is that there is no conventional device allowing for the intussusception, anastomosis and resection of the intussuscepted segment.

It is an object of the present invention to overcome the aforementioned drawbacks of the prior art and to provide an intraluminal anastomotic device which can intussuscept anastomosis and resect its segment of the colon, without exposing the dirty intraluminal content to the clean cavity achieved before the resection is completed. The present invention differs completely from the prior art devices because it is able to complete an anastomosis prior to the resection of the segment to be removed preventing the problem which can occur when the intraluminal contents (fecal material) contaminate the interior of the body cavity (e.g. the peritoneal cavity, thoracic cavity, etc.).

SUMMARY OF THE INVENTION

The objects of the present invention are achieved by an intraluminal reconstruction and resection device according to the present invention. The surgical device of the present invention includes a main housing adapted to be positioned within the bowel, a mechanism for first intussuscepting a segment of the bowel to be removed, a mechanism for anastomosis of the remaining portions of the bowel prior to the resection and a mechanism for resecting the intussuscepted segment of the bowel to be removed. The surgical device of the present invention additionally allows the resected portion of the bowel to be easily removed with the device. The preferred embodiment of the invention is directed to colon surgery, but the surgical device of the present invention can be applied to any hollow viscus surgery.

These and other objects of the present invention will be clarified in the Brief Description of the Preferred Embodiments taken together with the attached drawings wherein like elements represent like reference numerals throughout.

BRIEF DESCRIPTION OF THE PREFERRED EMBODIMENTS

Figure 1:
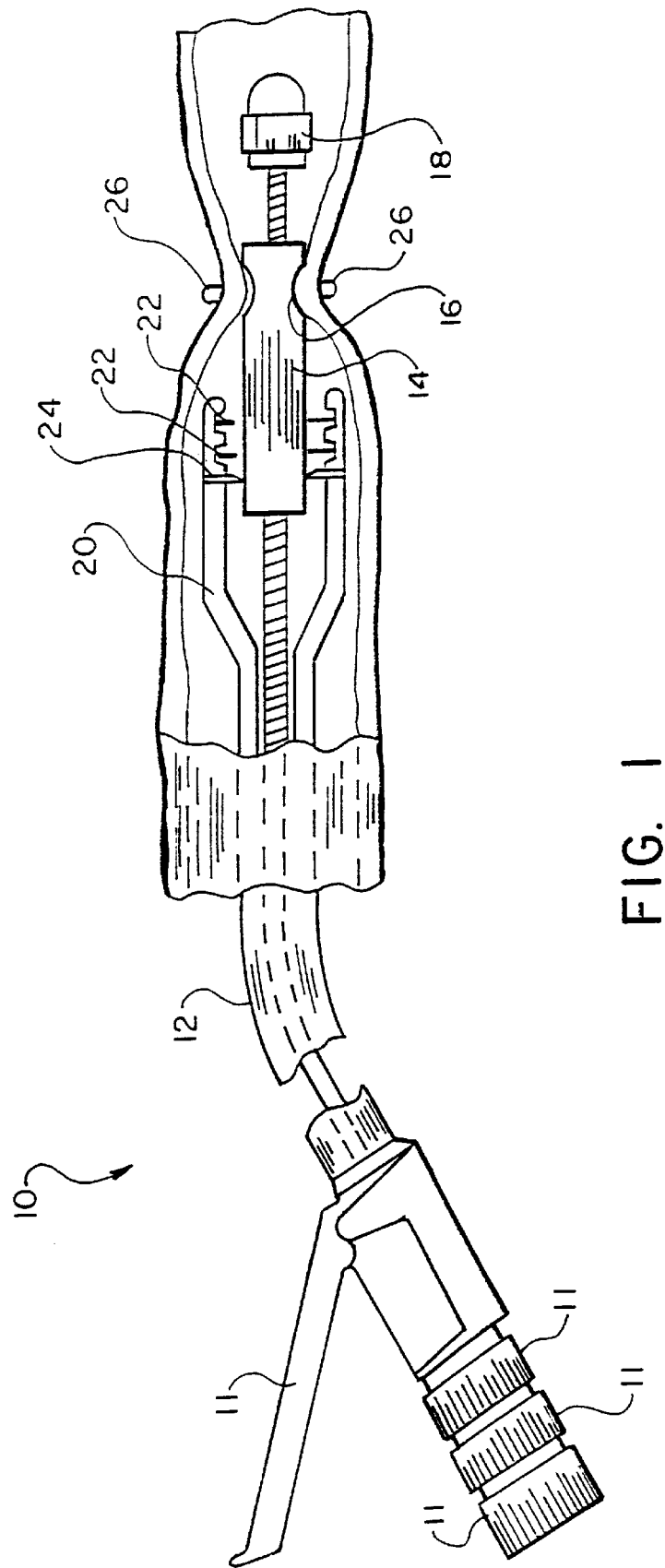
FIGS. 1–3 schematically illustrate an intraluminal intestinal reconstruction and resection device according to a first embodiment of the present invention with the device being illustrated in various operative positions.
Figure 2:
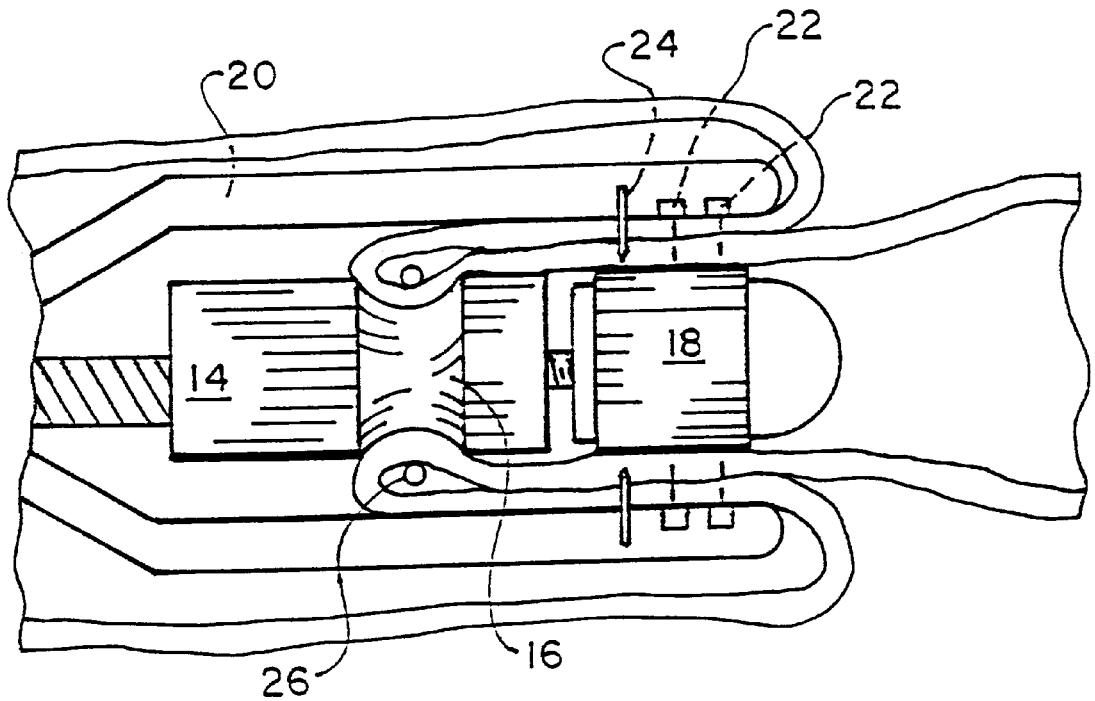
Figure 3:
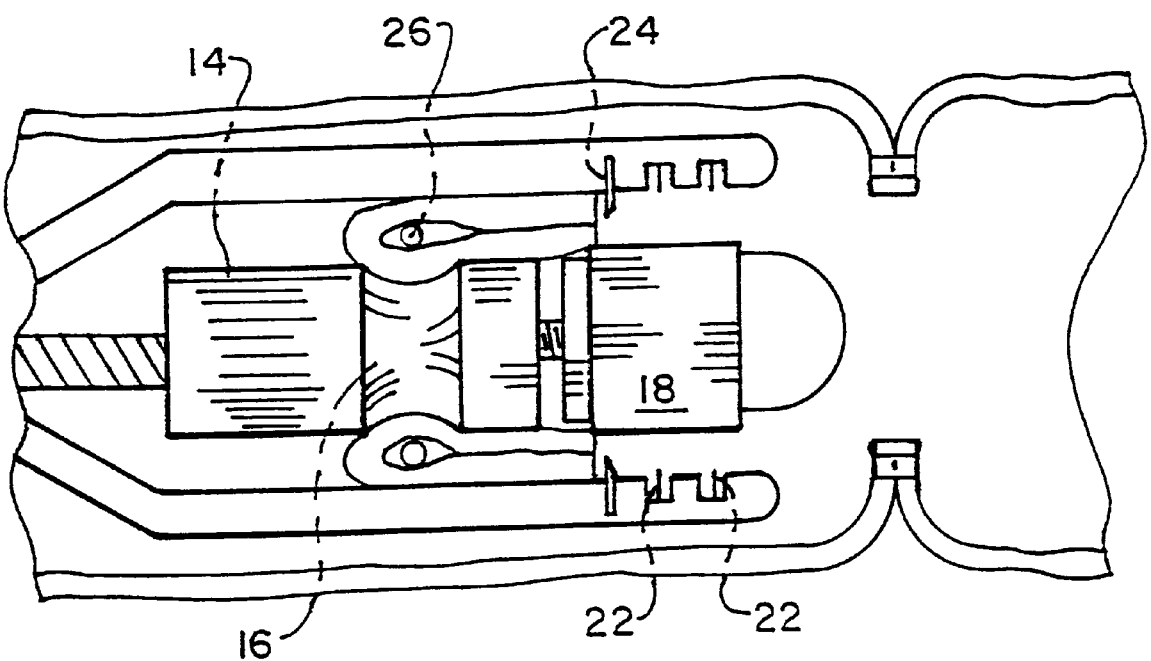

An intraluminal intestinal reconstruction and resection surgical tool 10 is illustrated schematically in FIGS. 1–3. The surgical tool 10 of the present invention is similar to end-to-end anastomosis staplers currently used in conventional colon resection and anastomosis techniques. The surgical tool 10 of the present invention is intended to be introduced into the bowel through the anus. The surgical tool 10 may also be introduced into the mouth or any other hollow viscus opening. Conventional operative controls 11 are positioned on the distal end of the tool 10 for control and operation by the surgeon. Similar to conventional flexible and rigid staplers, the surgical tool 10 includes a substantially cylindrical housing 12 extending from the handle at the distal end to the operative end of the surgical tool 10. The cylindrical housing 12 may be flexible or rigid. A central post 14 extends from the housing 12 substantially along the centerline of the housing 12. The central post 14 includes an annular groove 16 around the central post 14. The annular groove 16 is positioned on the central post 14 below an anvil member 18 which can be moved longitudinally relative to the central post 14 and controlled from below by an appropriate control 11.

An annular housing 20 extends from the housing 12 surrounding the central post 14. The annular housing 20 includes a pair of staple rows 22 shown schematically in FIGS. 1–3. In place of the staple rows 22, the annular housing 20 can include any attachment mechanism for anastomosis including mechanical connections such as staples, compression rings or biological connectors such as glue. The relative position of the staple rows 22 and the anvil member 18 may be reversed. Below the staple rows 22 is an annular knife 24 movable radially inwardly in a direction toward the central post 14. The knife 24 may also be positioned on the central post 14 for operating radially outwardly against the annular housing 20. In operation, a conventional firing or hammer mechanism (not shown) is utilized to fire staples in the staple rows 22 and move the annular knife 24 radially inward toward the central post 14 (or radially outward if the parts are reversed) as will be described hereinafter. The firing mechanism may be used to activate any other conventional connection for anastomosis procedure such as placing compression rings in place. Additionally, the central post 14 is movably mounted on the housing 12, such as by a threaded connection, such that the central post 14 is movable with respect to the annular housing 20 and anvil member 18. Alternatively, the annular housing 20 may be adjustable relative to the housing 12 to provide the adjustment between the annular housing 20, the central post 14 and the anvil member 18. It is anticipated that the annular housing 20, the anvil member 18 and the central post 14 may all be independently movable relative to the housing 12 to provide further movement between these elements. The movement of the central post 14, the anvil member 18, the annular housing 20 and control of the firing mechanism would be controlled by controls 11 at the distal end of the tool 10.

The operation of the surgical tool 10 according to a first embodiment of the present invention will be clarified by review of the sequential operation of the surgical tool 10 as is schematically illustrated in FIGS. 1–3. The surgical tool 10 of the present invention will be introduced into the bowel through the anus following the mobilization of the relevant portion of the colon. For other types of surgery, the tool 10 may be introduced into the mouth or any hollow viscus. The mobilization of the colon will be attended to in a conventional fashion and may be performed laparoscopically or through open surgery. Following the mobilization and resection of the mesentery, the surgical tool 10 is positioned into the bowel through the anus such that the annular groove 16 of the central post 14 is aligned midway along the segment of the colon to be resected. The bowel is attached to the central post 14, such as by tying the bowel portion to the central post 14 at the annular groove 16 with a ligation member 26. The annular groove 16 provides a receiving mechanism for the ligation member 26 which can be a conventional suture thread, a flexible band or the like surrounding the exterior of the bowel. The ligation of the bowel to the central post 14 can be accomplished laparoscopically or by open surgery. It is important that the ligation of the colon to the central post 14 be accomplished without compromising the bowel wall.

Following the ligation of the bowel to the central post 14, the central post 14 is moved relative to the annular housing 20 a distance approximately equal to one-half of the length of the bowel to be resected so that the cut mesentery come to a position proximate, one to the other. This movement can be accomplished by retraction of the central post 14 relative to the housing 12 or the advancement of the annular housing 20 relative to the central post 14 or the combination of both movements. With the bowel completely immobilized and attached to the central post 14, this relative movement will cause the intussusception of the segment of the bowel to be removed as shown in FIG. 2. Essentially, the segment to be removed will be drawn within the annular housing 20 and the cut mesentery will be drawn to a position proximate each other.

Following the intussusception of the segment of the bowel to be removed, the remaining bowel can be anastomosed, and the segment to be resected can be severed and withdrawn with the surgical tool 10. Preferably, the controls 11 will include an indication of the amount of relative movement, if any, between the annular housing 20 and the anvil member 18. This can be accomplished with incremental markings on the controls 11. The anvil member 18 is moved into alignment with the staple row 22 and annular knife 24. Preferably, the controls 11 will include indicia which can be used to identify when the anvil member 18 is in proper position relative to the annular housing 20. It is preferred that the annular housing 20 be clamped tightly against the anvil member 18 prior to the firing of the staples or advancement of the annular knife 24. This can be accomplished by using an expanding anvil member 18 formed by an overlapping ring of anvil material such as steel. The overlapping ring will allow the anvil member 18 to be expanded, as needed, by conventional mechanical, pneumatical or hydraulic mechanisms. Alternatively, the annular housing 20 can be constructed to constrict against the central post 14 and the anvil member 18 to achieve the appropriate clamping between the anvil member 18 and the annular housing 20. Following the clamping of the annular housing 20 against the anvil member 18, the staples in staple row 22 are fired, and the annular knife 24 is radially advanced against the anvil member 18 to sever the intussuscepted portion of the bowel. The staples and the knife 24 may be advanced simultaneously by the same firing mechanism (not shown) operated by an appropriate control 11 at the distal end of the tool 10. Even when operated simultaneously, the attachment of the remaining portions of the lumen will be considered to be prior to the completion of the resection by knife 24. In other words, simultaneous operation of the stapler 22 and the knife 24 will still effectively complete the anastomosis prior to completion of resection of the bowel. The firing mechanism would be a conventional actuator such as a longitudinally moving wedge-shaped member to advance the staples and the knife 24. As noted above, either/or both of the staples and knife 24 may be positioned and operated from anvil 18 to move radially outwardly against the annular housing 20.

The surgical tool 10 of the present invention illustrates the use of staples for anastomosis. Other attachment mechanisms can be utilized in the surgical tool 10 of the present invention. For example, compression rings may be utilized with opposed mating portions of the compression ring held on the annular housing 20 and the anvil member 18, respectively. The clamping mechanism for coupling the compression anastomosis would be substantially similar to the firing mechanism for the staples and for the advancement of the annular knife 24. Biological adhesive represents another attachment mechanism which could be utilized in the surgical tool 10. This can all be carried out with endoscopic guidance from optic fibers attached to the instrument.

Following the anastomosis of the bowel sections and the severing of the intussuscepted bowel segment, the surgical tool 10 can be withdrawn, as schematically illustrated in FIG. 3, bringing with it the resected portion of the bowel. The resected portion of the bowel remains attached to the tool 10 by ligation member 26 around central post 14. The surgical tool 10 of the present invention provides a simple mechanism for intussuscepting, reconstructing and resecting the bowel without exposing the clean body cavity to the dirty intraluminal portion of the bowel.

The surgical tool 10 of the present invention allows the anastomosis and resection of the bowel to also be performed in a minimally invasive environment. It is contemplated that fiber-optic viewing cables may be provided along the housing 12, central post 14, anvil member 18 and annular housing 20, as needed, in order to give the operator the appropriate direct views of the relative positioning of the elements of the surgical tool 10 and carry out the intraluminal procedure under direct vision. Optical fibers that are provided can be run back through the interior of the housing 12 to the distal end of the surgical tool 10 for connection to appropriate viewing screens as is known in the art.

One modification of the surgical tool 10 provides that the annular housing 20 may be applied from the exterior of the bowel at the point of resection. In this modification, the knife 24 would be replaced with a cutting loop for cutting the intussuscepting bowel portion. The construction of the cutting loop will similar to the cutting loop described below in connection with surgical tool 50. Another modification would be forming the anvil member 18 as a flat plate, or other shape, which may simplify the corresponding design of the housing 20.

FIGS. 4–8 schematically illustrate the operative end of a surgical tool 50 according to a second embodiment of the present invention. The surgical tool 50 is analogous to the surgical tool 10 described above and operates in a similar manner to carry out the intraluminal resection of the intestine. The surgical tool 50 includes a substantially cylindrical housing 52 extending from an operative end of the surgical tool 50 to the distal handle portion (not shown) of the tool 50. The handle portion of the tool will include conventional controls for controlling the operative end of the tool 50. A surgical tool 50 includes an annular groove 56 around the housing 52 with the annular groove 56 being analogous to the annular groove 16 on central post 14 of the surgical tool 10 described above. The annular groove 56 is provided to receive the ligation member 26 for attaching the bowel to the surgical tool 50 as will be described hereinafter.

The surgical tool 50 includes an anvil member 58 at a distal end of the surgical tool 50 which is movable relative to the stapling head 60. The anvil member 58 and stapling head 60 combine to form a stapling assembly 61 which is movable relative to at least the annular groove 56 of the housing 52 as will be described hereinafter. The anvil member 58, the stapling head 60 and the annular groove 56 are movable relative to each other similar to anvil member 18, annular housing 60 and central post 14 of tool 10. The stapling assembly 61 is substantially identical to the stapling assembly of conventional end-to-end anastomosis staplers and includes two annular staple rows 62 surrounding an annular knife 64. Staple rows 62 and annular knife 64 differ significantly from staple rows 22 and annular knife 24 of surgical tool 10 in that the staple rows 62 and annular knife 64 operate along the longitudinal length of the surgical tool 50 in the same manner as conventional end-to-end anastomosis stapling devices.

Figure 6:
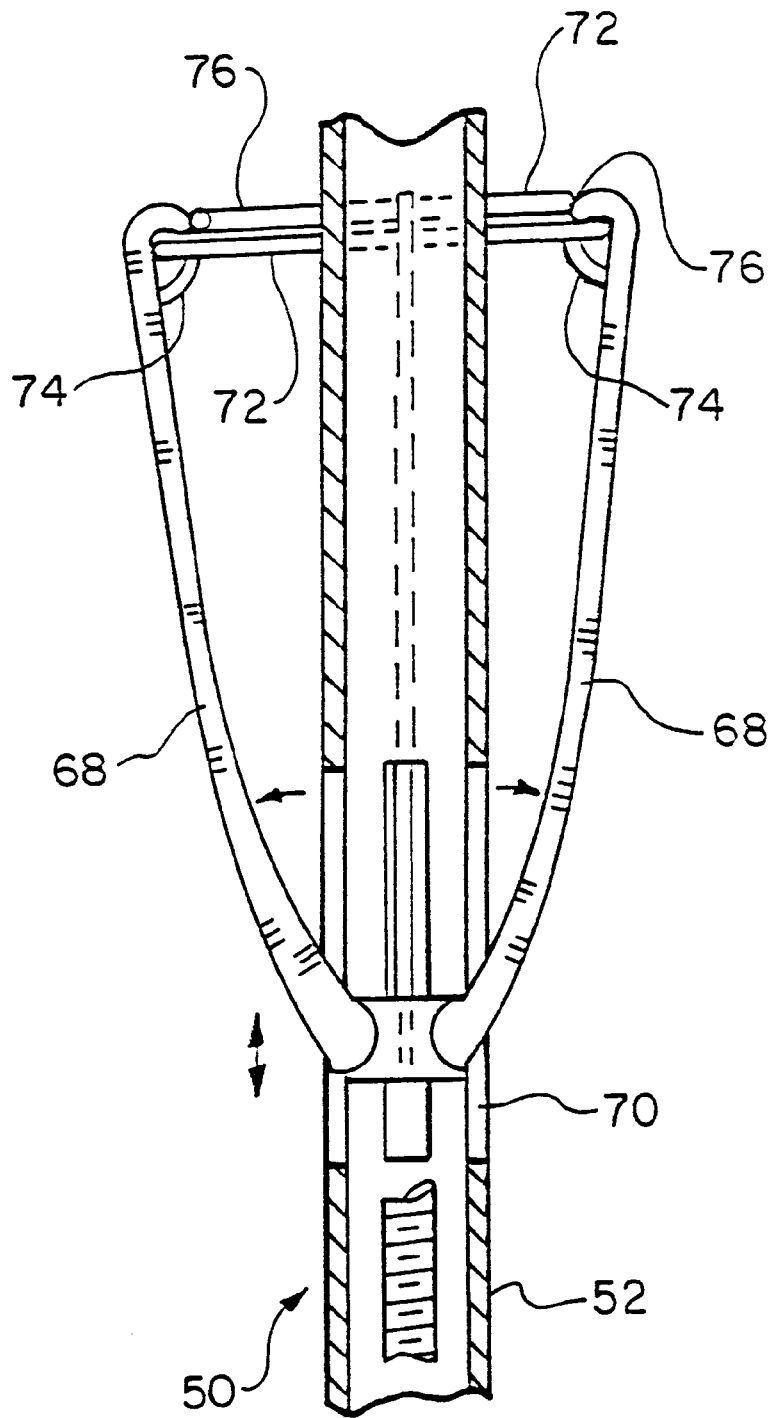

As shown schematically in FIG. 6, the housing 52 includes a plurality of carrier arms 68 which extend out of the housing 52 through slots 70. The carrier arms 68 may be completely exterior to the housing 52. The carrier arms 68 are movable relative to the housing 52 and are adapted to expand away from the housing 52 as the carrier arms 68 are moved toward the operative end of the surgical tool 50. The distal ends of the carrier arms 68 releasably hold an expandable band or loop 72. The expandable band 72 can be released from the carrier arms 68 by operation of a pivotable latch 74 preferably operated from the distal handle portion of the surgical tool 50. The carrier arms 68 additionally carry a severing wire 76 forming a constrictable loop about the housing 52. The movement of the carrier arms 68, release of the latch 74 and constricting of the wire 76 are additionally preferably controlled by lead wires or the like extending to actuators or controls at the distal handle end of the surgical tool 50.

Figure 4:
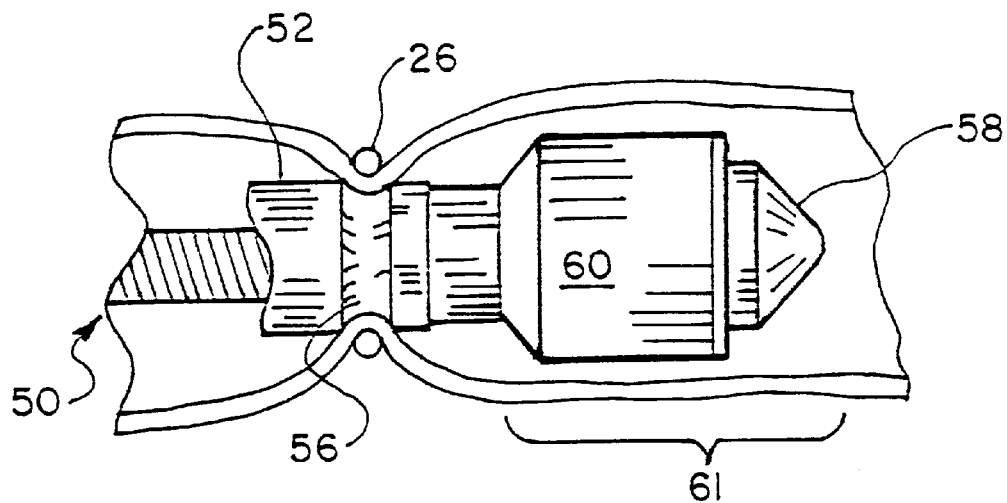
FIGS. 4–8 schematically illustrate an intestinal reconstruction and resection device according to a second embodiment of the present invention with the device illustrated in various operative positions.
Figure 5:
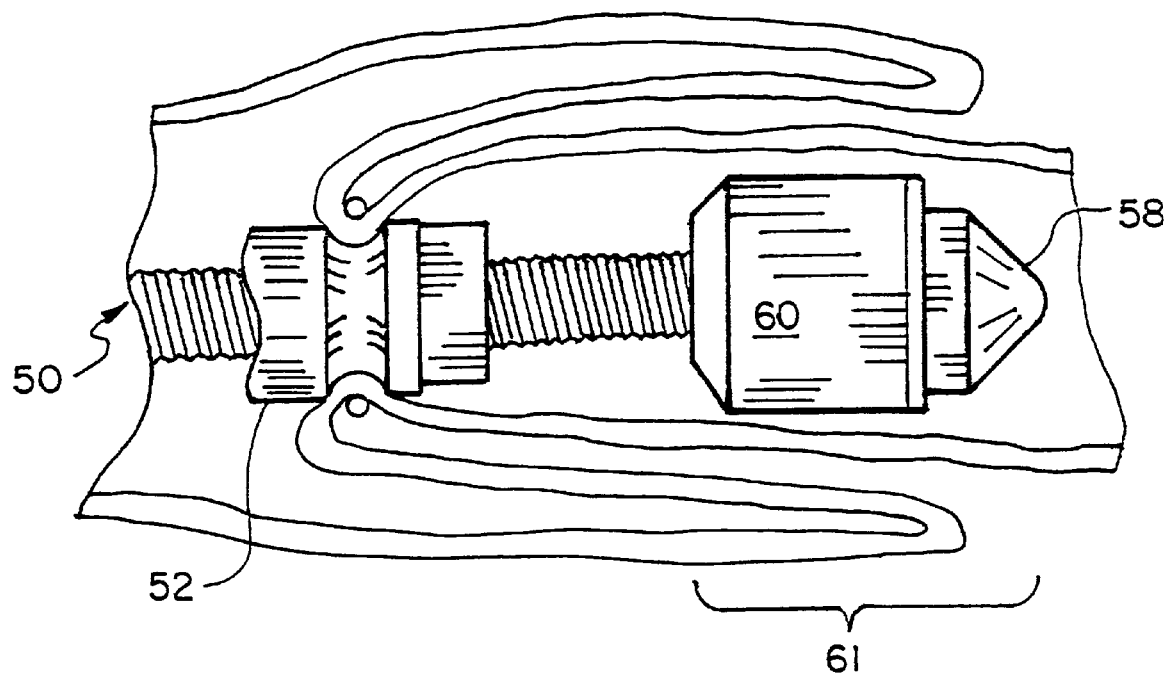

The surgical tool 50 operates as follows. The surgical tool 50 will be inserted through the anus following the mobilization of the colon. The annular groove 56 will be aligned substantially midway along the segment of the colon to be removed. The colon can then be attached to the housing 52 at the annular groove 56 with the ligation member 26, as shown in FIG. 4, substantially in the same manner as discussed above in connection with surgical tool 10. Following the attachment of the colon to the surgical tool 50, the portion of the colon to be resected is intussuscepted by relevant movement of the stapling assembly 61 relative to the annular groove 56 as shown in FIG. 5. In the surgical tool 50 illustrated in FIG. 5, the stapling assembly 61 is advanced relative to the housing 52 by a threaded connection. The relevant portion of the bowel will be intussuscepted by a withdrawal of the distal end of the surgical tool 50 corresponding to the advancement of the stapling assembly 61 relative to the annular groove 56 and housing 52.

Figure 7:
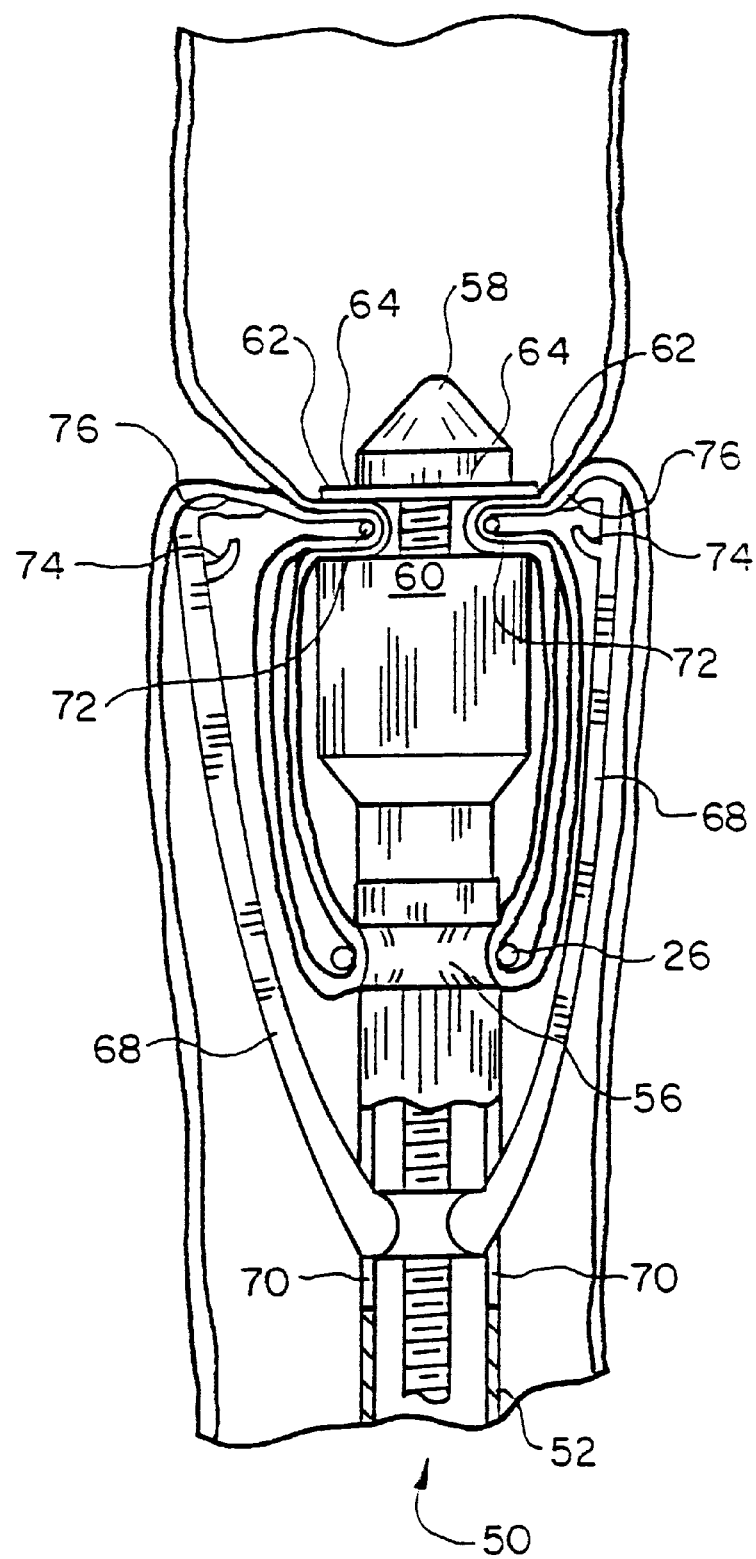
Figure 8:
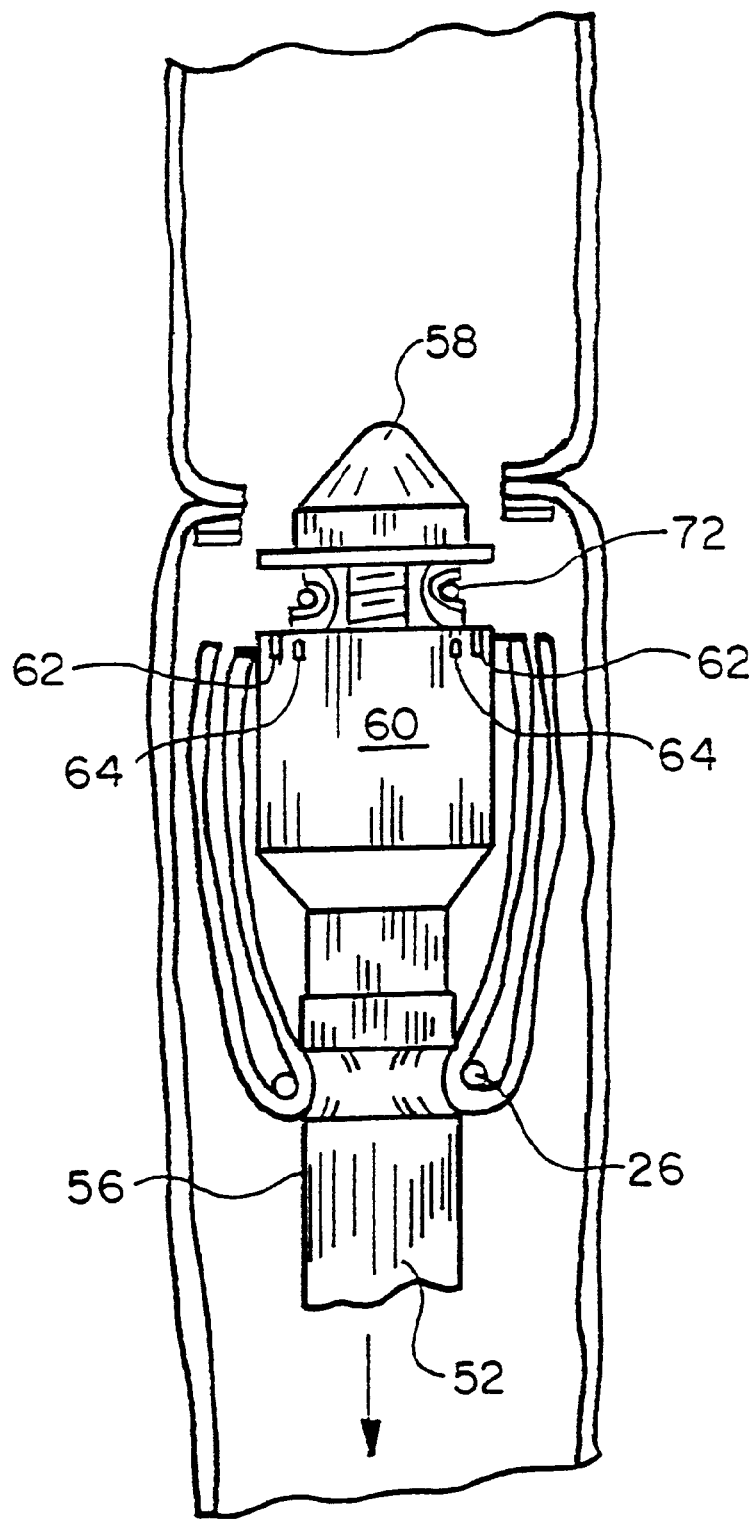

Following the intussusception of the bowel, the appropriate portions of the remaining ends of the bowel to be anastomosed must be positioned between the stapling head 60 and the anvil member 58. The expandable band 72 is utilized for proper positioning of the bowel members between the anvil member 58 and the stapling head 60. The carrier arms 68 are advanced to a position shown in FIG. 7 where the latch 74 can be used to release the expandable band or loop 72. Releasing of the expandable band 72 will pull the appropriate portions of the bowel between the anvil member 58 and the stapling head 60 such that these members can be proximated together in a conventional fashion as shown in FIG. 7.

In place of carrier arms 68 and expandable band 72, a nylon thread with a tightenable noose may be used. The thread will form a loop about the housing 52 and include a surrounding sheath extending to the noose which is used for both advancing the nylon loop and acting against the noose to tighten the loop. In operation, the sheath is advanced with the nylon thread to the desired position which will be generally the position of the carrier arms 68 shown in FIG. 7. The thread end extending through the sheath is then pulled to have the sheath act against the noose and have the loop tighten. The loop will constrict against the central rod and act substantially the same as the band 72. A trailing end of the thread will extend down the tool until it is severed during the cutting procedure. This arrangement may be less complex than the carrier arm 68 arrangement shown in the figures.

The stapling rows 62 together with the annular knife 64 can be fired or operated in a conventional fashion to perform the anastomosis of the respective pieces. Following the anastomosis, the severing wire 76 is positioned surrounding the stapling head 60 at a position below the anastomosis site. The wire 76 can be constricted around the stapling head 60 to sever the intussuscepted portion of the colon to be removed. If the carrier arms 68 are replaced with a nylon loop as discussed above, then wire 76 would be easily formed as a tightenable wire loop extending about the housing 52. The wire 76 may also be replaced with a radially outwardly extending knife positioned on stapler head 60 and acting against an annular anvil. Following the severing of the colon portion to be removed, the surgical tool 50 is withdrawn together with the intussuscepted, resected portion of the colon which remains attached to the surgical tool 50 by ligation member 26.

The severing wire 76 is utilized for removing the intussuscepted, resected portion of the bowel. The annular knife 64 is helpful for trimming of the bowel portion adjacent the anastomosis site and for allowing the expandable band 72 to be removed with the trimmed portions. The annular knife 64 can be eliminated if it is intended for the expandable band 72 to be maintained in place. The annular knife 64, if utilized for removing the expandable band 72, should be severing the bowel portions at a position radially between the expandable band 72 and the staple rows 62 as illustrated in FIG. 7. Where the band 72 is replaced with a nylon loop as described above, the annular knife 64 will sever the trailing end of the thread.

Surgical tool 50 is illustrated as using staples for connecting the respective portions of the bowel. Other mechanical or biological attaching mechanisms may be utilized in place of the staples such as compression rings, glue or the like.

Various optical fibers may be placed on the stapling assembly 61, the housing 52, the carrier arms 68 or the like to give the surgeon a direct view of the procedure. These fibers may extend down through the housing 52, or exterior thereto, and be connected to appropriate viewing screens in a conventional fashion.

It will be readily apparent to those of ordinary skill in the art that various changes may be made to the present invention without departing from the spirit and scope thereof. The scope of the present invention is defined by the appended claims and equivalents thereto.

What is claimed is:

1. A surgical intraluminal resection and reconstruction device comprising:
 a housing;
 a luminal attachment and intussusception means coupled to said housing for attachment and inversion of a portion of the lumen to be removed;
 a luminal anastomosis means coupled to said housing for attaching the lumen wall together prior to completion of resection; and
 a resection means coupled to said housing for severing the intussuscepted portion of the lumen after the anastomosis without opening the lumen.

2. The surgical device of claim 1 wherein said luminal anastomosis means and said resection means are movable relative to said luminal attachement and intussusception means.

3. The surgical device of claim 2 wherein said luminal attachment and intussusception means includes a central post adapted to have the lumen attached thereto.

4. The surgical device of claim 2 wherein said luminal attachment and intussusception means includes a groove on said housing.

5. The surgical device of claim 2 wherein said luminal anastomosis means includes a stapling head and an anvil.

6. The surgical device of claim 5 wherein said stapling head is an annular structure adapted to surround said anvil.

7. The surgical device of claim 5 wherein said resection device of claim 5 wherein said reception means includes a radially movable annular knife.

8. The surgical device of claim 5 wherein said stapling head includes two annular rows of staples adapted to fire against said anvil.

9. The surgical device of claim 1 further including a band for attaching the lumen to said luminal attachment and intussusception means.

10. The surgical device of claim 9 further including means coupled to said housing for holding said attachment band prior to use of said attachment band.

11. A surgical intraluminal resection and reconstruction device comprising:
 a housing;
 a luminal attachment and intussusception means coupled to said housing for attachment and inversion of a portion of the lumen to be removed; and
 a luminal anastomosis means coupled to said housing for attaching the lumen wall together prior to completeness of resection, wherein said luminal anastomosis means is movable relative to said luminal attachment and intussusception means.

12. The surgical device of claim 11 further including a resection means for severing the portion of the lumen to be removed wherein said resection means is adapted to resect the lumen substantially simultaneously with the attaching of the lumen wall by said anastomosis means.

13. The surgical device of claim 11 wherein said luminal anastomosis means includes a stapling head and anvil.

14. The surgical device of claim 13 wherein said stapling head is an annular structure adapted to surround said anvil.

15. A surgical intraluminal resection and reconstruction device comprising:
 a housing;
 a luminal attachment member coupled to said housing, said luminal attachment member adapted to have a lumen portion attached thereto; and
 a stapling assembly movable relative to said luminal attachment member, wherein relative movement between said stapling assembly and said luminal attachment member operates to invert a portion of the lumen.

16. The device of claim 15 wherein said luminal attachment member includes a movable central post.

17. The device of claim 15 wherein said luminal attachment member includes a groove in said housing.

18. The device of claim 15 further including a retractable knife for severing a portion of the lumen to be removed.

19. The device of claim 15 further including a band for attaching the lumen to said lumen attaching member and a carrier for said band.

20. The device of claim 15 further including a lumen severing wire for cutting a portion of the lumen to be removed.

* * * * *